(12) United States Patent
Buongiorno

(10) Patent No.: US 6,770,342 B2
(45) Date of Patent: Aug. 3, 2004

(54) MULTI-LAYER QUIET BARRIER FILM AND CONTAINER MADE THEREFROM

(75) Inventor: Livio Buongiorno, Via Parini (IT)

(73) Assignee: Sealed Air Corporation, Saddle Brook, NJ (US)

( * ) Notice: Subject to any disclaimer, the term of this patent is extended or adjusted under 35 U.S.C. 154(b) by 79 days.

(21) Appl. No.: 10/026,252

(22) Filed: Dec. 19, 2001

(65) Prior Publication Data

US 2002/0132071 A1 Sep. 19, 2002

(51) Int. Cl.$^7$ ............................ B32B 27/32; C08K 5/54
(52) U.S. Cl. .................... 428/36.6; 428/36.7; 428/36.8; 428/447
(58) Field of Search .............................. 428/36.6, 36.7, 428/36.8, 447

(56) References Cited

U.S. PATENT DOCUMENTS

| | | | |
|---|---|---|---|
| 4,535,113 A | * | 8/1985 | Foster et al. ................. 524/262 |
| 4,687,711 A | | 8/1987 | Vietto et al. ................. 428/515 |
| 5,043,205 A | | 8/1991 | Perazzo et al. ............. 428/215 |
| 5,091,453 A | | 2/1992 | Davidson et al. ........... 524/269 |

* cited by examiner

*Primary Examiner*—Sandra M. Nolan
(74) *Attorney, Agent, or Firm*—Thomas C. Lagaly

(57) ABSTRACT

A multi-layer gas- and odour-barrier film comprising a gas- and odor-barrier layer a) and at least one outer layer b) comprising a blend of an ethylene-vinyl acetate copolymer, an ethylene-alkyl-acrylate or alkyl-methacrylate copolymer and from about 1 to about 15% by weight on the overall weight of the blend of a silicone elastomer.

10 Claims, 1 Drawing Sheet

MULTI-LAYER QUIET BARRIER FILM AND CONTAINER MADE THEREFROM

BACKGROUND

The present invention relates to a gas- and odour-barrier multi-layer film with good properties of noiselessness as well as of softness and flexibility, and to the flexible containers intended for human drainage in medical applications made therewith.

For certain medical applications, containers, such as bags or pouches, are required for use in contact with the skin, under the patient's garments, for collecting excretion products from patients whose excretive apparatus has been deviated or reconstructed surgically following traumatic or pathological events. These containers or bags are generally referred to as "ostomy" pouches.

Films suitable for such a specific end use should meet a number of requirements: they must be gas- and odour-barrier; have mechanical properties that afford a good degree of protection against wear, abrasion and puncturing; possess quietness features that render the sound emission, particularly when the patients moves around, almost impossible to be perceived by a human ear; and softness and "feel" features that make them suited to applications involving compatibility with human skin. Furthermore they should be sealable, e.g. heat or RF sealable, so that no leakage, even minimal, occurs at the seal, and easily processable without giving any sticking problem.

Currently available from a number of manufacturers are excretion product collecting containers which meet some of the requirements set forth above.

In particular commercially available ostomy pouches, such as those with a PVDC gas- and odour-barrier core layer and outer layers of e.g. ethylene-vinyl acetate copolymers, typically have good mechanical and gas- and odour-barrier properties, good sealability and easily processable while they are generally poor in noiselessness and softness so that the patient is never allowed to at least occasionally "forget" his/her disabled condition, with obvious disturbing consequences of a psychological nature.

U.S. Pat. No. 5,043,205 describes a method to improve the softness and noiselessness of films for medical use by employing ethylene-butyl acrylate copolymers or blends of ethylene-butyl acrylate copolymers with an elastomeric polyolefin for the skin layers thereof.

BE-A-899,649 also describes films particularly suitable for use in ostomy applications wherein the outer skin layers comprise a mixture of ethylene-vinyl acetate copolymer, an elastomeric copolymer of ethylene and propylene and a hydrocarbon processing aid.

In these cases the improvement in softness and noiselessness is remarkable but the film is difficult to process and owing to the low Vicat temperature of the elastomer contained in the outer skin layers, it may easily stick to itself when wound up.

It has now been found that it is possible to obtain a film having high mechanical and gas- and odour-barrier properties, good sealability, good processability, and remarkable softness and noiselessness features, that can suitable be employed for ostomy applications, by providing a multi-layer film comprising a gas- and odour-barrier layer and at least an exterior layer comprising a blend of ethylene-vinyl acetate copolymer, ethylene-alkyl(meth)acrylate copolymer and at least 1% by weight of a silicone elastomer.

SUMMARY OF THE INVENTION

The first object of the present invention is a multi-layer gas- and odour-barrier film comprising a gas- and odour-barrier layer a) and at least one outer layer b) comprising a blend of an ethylene-vinyl acetate copolymer, an ethylene-alkyl-acrylate or alkyl-methacrylate copolymer and from about 1 to about 15% by weight calculated on the overall weight of the blend of a silicone elastomer.

A second object of the present invention is a bag or container intended in particular for human draining and collecting excretion products from patients having a deviated reconstructed excretive apparatus made with the film of the first object.

DEFINITIONS

Figure 1:
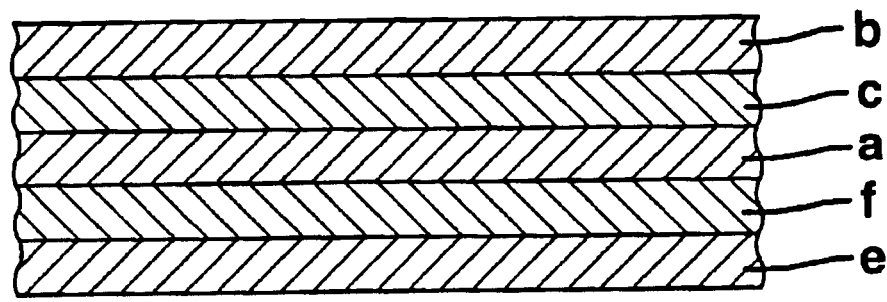
FIG. 1 is a side view of a five layer structure of the present invention

As used herein, the term "film" is used in a generic sense to include any flexible plastic web, regardless of whether it is film or sheet. Preferably, films of use in the present invention have a thickness of 250 $\mu$m or less, more preferably of 150 $\mu$m or less.

As used herein, the phrases "inner layer", "internal layer", or "intermediate layer" refer to any film layer having both of its principal surfaces directly adhered to another layer of the film.

As used herein, the term "core", and the phrase "core layer" refer to any internal film layer which has a primary function other than serving as an adhesive or compatibilizer for adhering two layers to one another.

As used herein, the term "barrier", and the phrase "barrier layer", as applied to films and/or film layers, is used with reference to the ability of a film or film layer to serve as a barrier to gasses and odours.

As used herein, the phrase "outer layer" or "exterior layer" refers to any film layer having less than two of its principal surfaces directly adhered to another layer of the film. In multi-layer films, there are two outer layers, each of which has a principal surface adhered to only one other layer of the multilayer film.

As used herein, the phrases "seal layer", "sealing layer", "heat seal layer", and "sealant layer", refer to an exterior film layer involved in the sealing of the film to itself, another film layer of the same or another film, and/or another article which is not a film.

As used herein, the term "seal" refers to any seal of a first region of a film surface to a second region of a film surface, wherein the seal is formed by heating the regions to at least their respective seal initiation temperatures. The heating can be performed by any one or more of a wide variety of manners, such as using a heated bar, hot air, infrared radiation, radio frequency radiation, etc.

As used herein, the phrase "directly adhered", as applied to film layers, is defined as adhesion of the subject film layer to the object film layer, without a tie layer, adhesive, or other layer there-between. In contrast, as used herein, the word "between", as applied to a film layer expressed as being between two other specified layers, includes both direct adherence of the subject layer to the two other layers it is between, as well as a lack of direct adherence to either or both of the two other layers the subject layer is between, i.e., one or more additional layers can be imposed between the subject layer and one or both the layers the subject layer is between.

As used herein, the term "polymer" refers to the product of a polymerization reaction, and is inclusive of homopolymers, copolymers, terpolymers, etc.

As used herein, the term "polyolefin" means a thermoplastic homo-, co- or ter-polymer derived from simple olefins, e.g. ethylene, propylene and higher unsaturated aliphatic monomer units, or the halogenated derivatives thereof, as well as the co- or ter-polymers of said simple olefins with co-monomers that are not themselves olefins, e.g. vinyl acetate, acrylic or methacrylic acids, salts, or esters, provided however that the olefin comonomer is present in a major amount. More specifically, included in the term polyolefin are homopolymers of olefins, copolymers of olefins, copolymers of an olefin and a non-olefinic comonomer copolymerizable with the olefin, such as vinyl monomers, and the like. Heterogeneous and homogeneous polymers are included. Specific examples include polyethylene homopolymers, poly-butene, propylene-α-olefin copolymers, ethylene-α-olefin copolymers, butene-α-olefin copolymers, ethylene-vinyl acetate copolymers, ethylene-ethyl acrylate copolymers, ethylene-butyl acrylate copolymers, ethylene-methyl acrylate copolymers, ethylene-acrylic acid copolymers, ethylene-methacrylic acid copolymers, ionomers, chlorinated polyethylene, etc.

As used herein, the phrase "heterogeneous polymer" refers to polymerization reaction products of relatively wide variation in molecular weight and relatively wide variation in composition distribution. Such polymers typically contain a relatively wide variety of chain lengths and comonomer percentages.

As used herein, the phrase "homogeneous polymer" refers to polymerization reaction products of relatively narrow molecular weight distribution and relatively narrow composition distribution. Homogeneous polymers exhibit a relatively even sequencing of comonomers within a chain, the mirroring of sequence distribution in all chains, and the similarity of length of all chains.

As used herein, the phrase "ethylene-α-olefin copolymer" refers to such heterogeneous materials as linear low density polyethylene (LLDPE), and very low and ultra low density polyethylene (VLDPE and ULDPE); and homogeneous polymers such as Ziegler-Natta-catalyzed homogenous polymers, for example TAFMER™ materials supplied by Mitsui Petrochemical, and metallocene-catalyzed homogenous polymers, such as EXACTS™ materials supplied by Exxon, AFFINITY™ or ENGAGE™ resins supplied by Dow, or LUFLEXEN™ materials supplied by BASF.

As used herein the term "modified polyolefins" include modified polymers prepared by copolymerizing the homopolymer of the olefin or copolymer thereof with an unsaturated carboxylic acid, e.g., maleic acid, fumaric acid or the like, or a derivative thereof such as the anhydride, ester or metal salt or the like, or by incorporating into the olefin homopolymer or copolymer, an unsaturated carboxylic acid, e.g., maleic acid, fumaric acid or the like, or a derivative thereof such as the anhydride, ester or metal salt or the like.

As used herein, the phrase "tie layer" refers to any internal layer having the primary purpose of adhering two layers to one another. Tie layers generally comprise a non-polar or slightly polar polymer having a polar group grafted thereon; preferably, tie layers comprise at least one member selected from the group consisting of polyolefin and modified polyolefin, e.g. ethylene-vinyl acetate copolymer, modified ethylene-vinyl acetate copolymer, heterogeneous and homogeneous ethylene-α-olefin copolymer, and modified heterogeneous and homogeneous ethylene-α-olefin copolymer; more preferably, tie layers comprise at least one member selected from the group consisting of anhydride grafted linear low density polyethylene, anhydride grafted low density polyethylene, homogeneous ethylene-α-olefin copolymer, and anhydride grafted ethylene-vinyl acetate copolymer.

DETAILED DESCRIPTION OF THE INVENTION

In the film according to the present invention at least one outer layer b) comprises a blend of an ethylene-vinyl acetate copolymer, an ethylene-alkyl-acrylate or alkyl-methacrylate copolymer and from about 1 to about 15% by weight on the overall weight of the blend of a silicone elastomer.

Said outer layer b) will be the film layer that in the container for ostomy applications will be in contact with the patient skin.

Ethylene-vinyl acetate copolymers that may suitably be employed for the outer layer b) will generally contain up to about 40% of vinyl acetate units. Ethylene-vinyl acetate copolymers with from about 14 to about 35% of vinyl acetate units are preferred while ethylene-vinyl acetate copolymers with from about 18 to about 30% of vinyl acetate units are even more preferred. The amount of ethylene-vinyl acetate copolymer in the blend may range from about 10 to about 90% by weight, preferably from about 20 to about 80 and even more preferably from about 30 to about 70% by weight on the overall weight of the blend.

Any ethylene-($C_1$–$C_4$)alkyl-acrylate or alkyl-methacrylate copolymer, commercially available can suitably be employed in the manufacture of the film according to the present invention. These copolymers typically contain ethylene derived units in major amounts and the alkyl (meth)acrylate derived units in minor amounts, preferably from about 2% to about 28% by weight, and more preferably from about 4 to about 18% by weight. While these copolymers are preferably ethylene-methyl acrylate or ethylene-methyl-methacrylate copolymers, other copolymers such as e.g. ethylene-ethyl acrylate, ethylene-isobutyl-methacrylate, and ethylene-n-butyl-acrylate copolymers can suitably be employed.

The amount of ethylene-alkyl-acrylate or methacrylate copolymer in the blend will be typically comprised between about 10 and about 70% by weight, preferably between about 20 and about 60 and more preferably between about 30 and about 50% by weight on the overall weight of the blend.

The third component of the blend is a silicone elastomer or—as it is often referred to—a silicone rubber, i.e. a high molecular mass polyorganosiloxane rubber, with a molecular mass in the range of from about $3 \times 10^5$ to about $10^6$. The basic polymer of this class is polydimethylsiloxane (dimethylsilicone elastomer) having a substantially linear molecular structure with the following composition [—$(CH_3)_2SiO$—]$_n$. A small part of the methyl group in the above formula may be substituted with higher alkyl or with phenyl groups.

In a preferred embodiment of the present invention the silicone elastomer blended into the outer layer b) is polydimethylsiloxane.

The silicone elastomer needs to be present in an amount of at least 1% by weight, preferably in an amount of at least 2% by weight, and even more preferably in an amount of at least 2.5% by weight, up to a maximum of about 15% by weight on the overall weight of the blend. It is generally added as a masterbatch wherein said silicone elastomer is dispersed in a resin carrier that maybe one of the thermoplastic polymers of the blend, e.g. EVA or an ethylene-alkyl-acrylate or methacrylate, or any other polyolefin, such as a polyethylene or a linear polyethylene. The masterbatch typically will contain the silicone elastomer in amounts of from about 25 to about 75% by weight. The use of a masterbatch is preferred as the distribution of the silicone elastomer within the blend will be uniform. It is however also possible to avoid the use of the masterbatch and add the silicone elastomer directly to the other components of the blend in a compounding line. The amount by weight indicated above for the silicone elastomer, from about 1 to about 15%, refers to the pure product. Thus, if a masterbatch containing 50% of silicone elastomer is employed, the amount thereof will be comprised between about 2 and about 30% by weight calculated on the overall weight of the blend.

A preferred blend for the outer layer b) of a film according to the present invention comprises from about 50 to about 75 parts by weight of ethylene-vinyl acetate copolymer, from about 25 to about 50 parts by weight of an ethylene alkyl-acrylate or methacrylate copolymer and from about 1 to about 15 parts by weight of silicone elastomer.

In a preferred embodiment of the present invention the above blend will make up at least a major proportion of the outer layer b), i.e., more than 50%, preferably more than 75%, and even more preferably more than 90% by weight calculated on the weight of the outer layer b), and in a most preferred embodiment said outer layer b) will essentially consist of the above blend.

The thickness of said outer layer is not critical and will depend on the overall thickness desired for the film and on the number of layers present in the structure. Typically however the thickness of said outer layer b) will be comprised between about 8 and about 70 µm, preferably between about 15 and about 60 µm and even more preferably between about 20 and about 50 µm.

The gas- and odour-barrier layer a) preferably comprises a vinylidene chloride copolymer with a comonomer selected from vinyl chloride, acrylic esters, and acrylic acid (PVDC) or a blend thereof. Said resin may be suitably additivated as known in the art to render it as soft as possible while maintaining optimum gas- and odour-barrier properties.

The gas- and odour-barrier layer a) may alternatively comprise anyone of the other conventional materials, normally used for this purpose, such as, polyamides, ethylene-vinyl alcohol copolymers, blends of ethylene-vinyl alcohol and polyamide, or polyvinyl alcohols.

The thickness of the barrier layer a) can vary from about 3 to about 20 µm, typically ranging from about 4 to about 15 µm, and more preferably from about 5 to about 12 µm.

An intermediate layer c) may be positioned between the gas- and odour-barrier layer a) and the outer layer b) to increase the bond between these two layers and/or to increase the bulk and the mechanical properties of the structure. In a preferred embodiment, when the gas- and odour-barrier layer a) comprises PVDC, said intermediate layer will comprise an ethylene-vinyl acetate copolymer and more preferably an ethylene-vinyl acetate copolymer with a high vinyl acetate content, e.g. from 14 to 40 or more %, preferably from 18 to 30%, even more preferably from 22 to 28% of vinyl acetate units or an EVM-elastomer, i.e. an ethylene-vinyl acetate copolymer where the % of vinyl acetate units are typically comprised between about 40 and about 75. Using an EVA with a high content of vinyl acetate units it is possible to increase the bulk of the structure with a fairly cheap polymer, endowed with a high softness and noiselessness, that improves the RF-sealability of the overall structure, if this is desired, and provides for a good bond between the PVDC barrier layer a) and the outer layer b).

Other polymer resins that may suitably be admixed with the EVA or replace the EVA in said optional intermediate layer c), include ethylene-acrylic acid copolymers, ethylene-methacrylic acid copolymers, the esters thereof, homogeneous and heterogeneous LLDPE, VLDPE and ULDPE, etc.

If the barrier polymer of layer a) is an ethylene-vinyl alchol copolymer or a polyamide, the intermediate layer c) may be employed to increase the bulk of the structure while a separate tie layer d) may be necessary to guarantee a good bond between the gas-barrier layer a) and the outer layer b) or the intermediate bulk layer c). In such a case the tie layer d) will preferably comprise a modified polyolefin, such as an anhydride grafted ethylene-vinyl acetate copolymer or an anhydride grafted heterogeneous or homogeneous LLDPE, VLDPE or ULDPE, or an EVM-elastomer as known in the art.

In a preferred embodiment of the present invention the gas- and odour-barrier layer is a core layer and the film has at least another outer layer e).

The other outer layer e), that in the final container will be the innermost layer and that therefore does not need to have softness and "hand-feel", can be made with any sealable polyolefin or polyolefin blend. If RF-sealability is required, it will preferably comprise a polar ethylene copolymer, such as EVA, to provide for the RF-sealability.

In a more preferred embodiment however also the outer layer e) will comprise a blend of an ethylene-vinyl acetate copolymer, an ethylene-alkyl-acrylate or -methacrylate copolymer and from about 1 to about 15% by weight calculated on the overall weight of the blend of a silicone elastomer.

The thickness of said layer will typically be comprised between about 8 and about 70 µm, preferably between about 15 and about 60 µm, and even more preferably between about 20 and about 50 µm.

In a yet more preferred embodiment of the present invention the film has a substantially symmetrical structure where both outer layers have substantially the same composition, whereas they may differ for instance in the presence and/or amount of the additives.

An intermediate layer f), defined as the intermediate layer c) above, may be positioned between the outer layer e) and the core gas- and odour-barrier layer a).

If necessary or desirable, a tie layer g) may be positioned between the core gas- and odour-barrier layer a) and the intermediate layer f). Said tie layer g) is defined as the tie layer d) above.

In a most preferred embodiment the film is symmetrical.

In one embodiment, illustrated in FIG. 1, the film is a 5-layer film wherein two intermediate layers c) and f) are present having one surface directly adhered to the opposite surfaces of the core gas- and odour-barrier layer a) and the other surface directly adhered to the inner surfaces of the outer layers b) and e) respectively.

Figure 2:
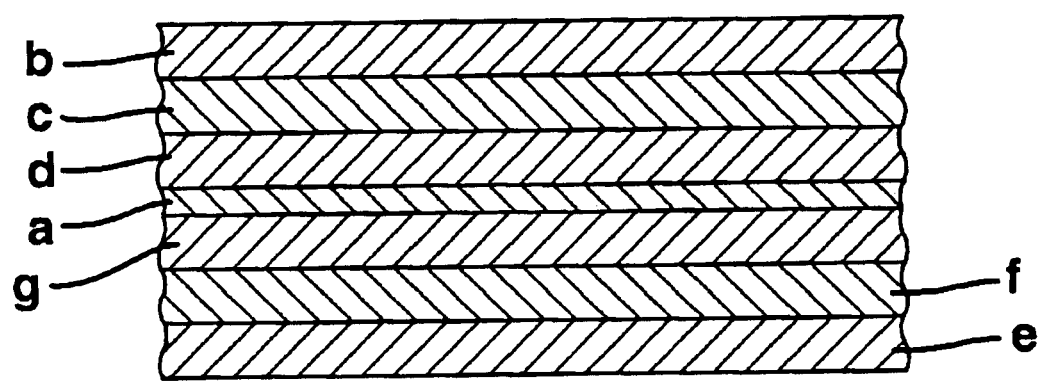
FIG. 2 is a side view of a seven layer structure of the present invention

In another embodiment, illustrated in FIG. 2, the film is a 7-layer film wherein two tie layers d) and g) are present to adhere the intermediate layers c) and f) respectively to the core gas- and odour-barrier layer a).

Opacifying additives and pigments can be included in one or more layers of the film, preferably the exterior layers to obtain an opaque, white or coloured, film.

Other additives, such as for instance antiblock and slip agents, UV absorbers, antimicrobial, stabilisers, anti-oxidant agents, etc., can also be included as known in the art.

The film according to the present invention can be obtained by means of conventional technology, for example by hot-blown, i.e. by coextrusion of the multilayer film through a circular die with multiple concentric slots, using the insufflation of a bubble of cold air while the polymers are still in the molten phase, or by cast coextrusion, either through a round or a flat die, according to methods known per se in this field. In all these methods the film is not stretched or oriented, at least intentionally. A slight orientation, so-called accidental orientation, may be present depending on the production method employed.

If desired, the end film thus obtained can be embossed in order to further improve the patient's comfort.

The examples which follow, only purport to illustrate the invention and not to restrict its field of application.

EXAMPLES

The following abbreviations have been used

EVA1=ethylene-vinyl acetate copolymer with 28% VA, MFI=3.5 g/10' (as determined by ASTM D-1238—Condition E) marketed by ATOFINA as EVATANE™ 28-25;

EVA2=ethylene-vinyl acetate copolymer with 28% VA, MFI=4.0 g/10' (as determined by ASTM D-1238—Condition E) marketed by ATOFINA as EVATANE™ 2803;

EVA3=ethylene-vinyl acetate copolymer with 18% VA, MFI=0.7 g/10' (as determined by ASTM D-1238—Condition E) marketed by DuPont as ELVAX™ 3165 containing about 0.5% erucamide and about 0.5% silica;

EMA1=ethylene-methyl acrylate copolymer with 14% MA, MFI=2.5 g/10' (as determined by ASTM D-1238—Condition E) marketed by ATOFINA as Lotryl 14MG02;

EMA2=ethylene-methyl acrylate copolymer with 17% MA, MFI=2.4 g/10' (as determined by ASTM D-1238—Condition E) marketed by Gulf as POLY-ETH 2255;

PDMS1=a blend of 25 wt. % of ultra high molecular weight polydimethylsiloxane (with viscosity (kinematic)=60,000 cSt) in linear low density polyethylene with MFI=4.0 g/10' (as determined by ASTM D-1238—Condition E) and d=1.0 g/cm$^3$ marketed by Dow Corning;

PDMS2=a blend of 50 wt. % of ultra high molecular weight polydimethylsiloxane (with viscosity (kinematic)=60,000 cSt) in EVA3 marketed by Dow Corning;

PVDC1=VDC-VC copolymer marketed by Solvay as IXAN XV 400 OF, added with 1% of hydrotalcite and 1% of epoxidised soya bean oil;

PVDC2=VDC-VC copolymer marketed by Solvay as IXAN XV 400, added with 1% of hydrotalcite and 1% of epoxidised soya bean oil;

MB1=masterbatch with EVA1 as the carrier and containing about 21% of $CaCO_3$ and about 15% of $SiO_2$ and $TiO_2$;

MB2=masterbatch with EVA2 as the carrier and containing about 20% of $TiO_2$ and 10% of tan pigments;

VLDPE1=ethylene-α-olefin copolymer with d=0.911 g/cm$^3$ and MFI=6.5 g/10' (as determined by ASTM D-1238—Condition E) marketed by DSM as Stamylex 08-076F.

VLDPE2=ethylene-α-olefin copolymer with d=0.902 g/cm$^3$ and MFI=1.0 g/10' (as determined by ASTM D-1238—Condition E) marketed by The Dow Chemical Company as AFFINITY™ PL1880.

Examples 1 to 16

5-layer Symmetrical Films Having the General Structure A/B/C/B/A wherein the composition and thickness of the A, B, and C layers are as indicated in Table 1 below, are prepared by the hot blown process.

The films are then converted into ostomy pouches by conventional heat-sealing.

TABLE 1

| Ex. no. | A | B | C |
|---|---|---|---|
| 1 | 35% EMA1<br>40% EVA2<br>5% PDMS1<br>20% MB1 (25 μm) | EVA1 (10 μm) | PVDC2 (5 μm) |
| 2 | 35% EMA1<br>40% EVA2<br>5% PDMS1<br>20% MB1 (25 μm) | EVA1 (10 μm) | PVDC1 (5 μm) |
| 3 | 35% EMA1<br>50% EVA2<br>10% PDMS1<br>5% MB2 (25 μm) | EVA1 (10 μm) | PVDC2 (5 μm) |
| 4 | 35% EMA1<br>50% EVA2<br>10% PDMS1<br>5% MB2 (25 μm) | EVA1 (10 μm) | PVDC1 (5 μm) |
| 5 | 35% EMA1<br>50% EVA2<br>10% PDMS2<br>5% MB2 (25 μm) | EVA1 (10 μm) | PVDC1 (10 μm) |
| 6 | 50% EMA1<br>35% EVA2<br>10% PDMS2<br>5% MB2 (25 μm) | EVA1 (10 μm) | PVDC1 (5 μm) |
| 7 | 65% EMA1<br>20% EVA2<br>5% PDMS2<br>20% MB1 (25 μm) | EVA1 (10 μm) | PVDC1 (5 μm) |
| 8 | 50% EMA1<br>25% EVA2<br>5% PDMS2<br>20% MB1 (25 μm) | EVA1 (10 μm) | PVDC1 (5 μm) |
| 9 | 35% EMA2<br>40% EVA3<br>20% PDMS1<br>5% MB2 (25 μm) | EVA1 (10 μm) | PVDC2 (5 μm) |
| 10 | 65% EMA1<br>20% EVA2<br>15% PDMS2<br>15% MB1 (25 μm) | EVA1 (10 μm) | PVDC1 (5 μm) |
| 11 | 50% EMA1<br>25% EVA2<br>20% PDMS2<br>5% MB2 (25 μm) | EVA1 (10 μm) | PVDC1 (5 μm) |
| 12 | 35% EMA2<br>45% EVA3<br>20% PDMS1 (25 μm) | EVA1 (10 μm) | PVDC2 (5 μm) |
| 13 | 40% EMA2<br>45% EVA3<br>15% PDMS1 (25 μm) | EVA1 (10 μm) | PVDC2 (5 μm) |
| 14 | 40% EMA2 | EVA1 (10 μm) | PVDC2 (5 μm) |

TABLE 1-continued

| Ex. no. | A | B | C |
|---|---|---|---|
| 15 | 40% EVA3<br>20% PDMS2 (25 μm)<br>40% EMA2<br>50% EVA3<br>10% PDMS1 (25 μm) | EVA1 (10 μm) | PVDC2 (5 μm) |
| 16 | 45% EMA2<br>45% EVA3<br>10% PDMS1 (25 μm) | EVA1 (10 μm) | PVDC2 (5 μm) |

Examples 17 to 20

7-layer symmetrical films having the general structure A/D/B/C/B/D/A wherein the composition and thickness of the A, B, C and D layers are as indicated in Table 2 below, are prepared by the hot blown process.

TABLE 2

| Ex. no. | A | B | C | D |
|---|---|---|---|---|
| 17 | 35% EMA1<br>45% EVA2<br>10% PDMS2<br>10% MB1 (20 μm) | EVA1<br>(15 μm) | PVDC2<br>(5 μm) | VLDPE1<br>(10 μm) |
| 18 | 35% EMA1<br>40% EVA1<br>5% PDMS1<br>20% MB1 (30 μm) | EVA1<br>(15 μm) | PVDC1<br>(5 μm) | VLDPE2<br>(5 μm) |
| 19 | 35% EMA1<br>40% EVA1<br>10% PDMS1<br>5% MB2 (30 μm) | EVA1<br>(10 μm) | PVDC2<br>(10 μm) | VLDPE1<br>(10 μm) |
| 20 | 30% EMA1<br>40% EVA2<br>15% PDMS2<br>15% MB1 (35 μm) | EVA1<br>(10 μm) | PVDC1<br>(5 μm) | VLDPE1<br>(5 μm) |

Quietness or absence of noise of representative examples of the film according to the present invention has been evaluated by a noise emission test specifically designed for ostomy pouches.

Said test is based on the simulation of the stresses applied by ostomates' body on ostomy pouches during everyday activities.

The pouches tested are moved (torsion/compression) by a device that applies to the pouch an axial stroke simultaneously with a 1800 rotation at the frequency of 30 cycles/min.

Each pouch is partially filled with a cylinder of porous material (a rectangle of flexible polyethylene foam 210 mm long, 85 mm wide and 3 mm thick, wounded around itself) fixed by a metallic clip on the pouch mouth.

The noise generated by the ostomy pouch under such stresses is measured in an anechoic room with a microphone positioned at 150 mm from the middle of the pouch to be tested. The tests are run at a temperature of about 22° C. and a relative humidity of about 50%. Five pouches are tested for each formulation and 5 measurements were made for each pouch. The equipment employed was manufactured by Brüel & Kjaer (i.e. Sound Level Calibrator, model 4231, Real Time Frequency Analyzer, model 2143, Microphone, model 4133, and Microphone Preamplifier, model 2639)

The applicable standards were IEC651 and IEC804. The measurements performed were the equivalent continuous sound pressure level (Leq), frequency weighing A, and the Sound Pressure Level with Impulse average time, frequency weighing A.

The results obtained in these tests with the film of Examples 1 and 3 are reported in Tables 3 to 6 below

TABLE 3

Film of Example 1

| Measurement n. | Tot. Leq dB[A]<br>To: 6':40" | Max dB[A] | Freq Hz |
|---|---|---|---|
| 1 | 47.3 | 47.3 | 3150 |
| 2 | 49.3 | 49.3 | 5000 |
| 3 | 46.0 | 46.0 | 2500 |
| 4 | 47.3 | 47.3 | 2500 |
| 5 | 47.3 | 47.3 | 2500 |
| Average | 47.4 | | |
| Std. Dev. | 1.2 | | |

TABLE 4

Film of Example 1

| Measurement n. | Tot. SPL dB[A]<br>Impulse | Max dB[A] | Freq Hz |
|---|---|---|---|
| 1 | 56.7 | 48.7 | 3150 |
| 2 | 56.3 | 45.9 | 2500 |
| 3 | 55.9 | 45.8 | 2500 |
| 4 | 56.6 | 48.3 | 4000 |
| 5 | 57.5 | 52.6 | 4000 |
| Average | 56.6 | | |
| Std. Dev. | 0.6 | | |

TABLE 5

Film of Example 3

| Measurement n. | Tot. Leq dB[A]<br>To: 6':40" | Max dB[A] | Freq Hz |
|---|---|---|---|
| 1 | 48.1 | 48.1 | 4000 |
| 2 | 47.4 | 47.4 | 4000 |
| 3 | 47.3 | 47.3 | 2500 |
| 4 | 46.9 | 46.9 | 2000 |
| 5 | 47.7 | 47.7 | 3150 |
| Average | 47.5 | | |
| Std. Dev. | 0.5 | | |

TABLE 6

Film of Example 3

| Measurement n. | Tot. SPL dB[A]<br>Impulse | Max dB[A] | Freq Hz |
|---|---|---|---|
| 1 | 58.0 | 50.0 | 4000 |
| 2 | 58.7 | 50.5 | 4000 |
| 3 | 59.4 | 51.3 | 5000 |
| 4 | 57.1 | 43.4 | 3150 |
| 5 | 58.3 | 50.4 | 4000 |
| Average | 58.3 | | |
| Std. Dev. | 0.8 | | |

The added features of sealability, resistance to wear, abrasion, and puncturing, as well as gas and odour barrier capabilities, qualify the films according to the present invention for use in the manufacture of containers, e.g. bags and pouches, for medical applications, especially for draining and collecting excretion products from stomized patients.

What is claimed is:

1. A multi-layer gas- and odour-barrier film comprising
    (a) a gas- and odour-barrier layer; and
    (b) at least one outer layer comprising a blend of (1) an ethylene-vinyl acetate copolymer,
(2) an ethylene/alkyl-acrylate or ethylene/alkyl-methacrylate copolymer, and
(3) a silicone elastomer, said elastomer being present in said blend at a weight percentage ranging from about 1 to about 15%, based on the overall weight of the blend, and having a molecular mass in the range of from about $3 \times 10^5$ to about $10^6$.

2. The film of claim 1, wherein the amount of ethylene-vinyl acetate copolymer in the blend of layer b) is from about 10 to about 90% by weight, based on the overall weight of the blend, and the amount of ethylene/alkyl-acrylate or ethylene/alkyl-methacrylate copolymer in the blend of layer b) is from about 10 to about 70% by weight, based on the overall weight of the blend.

3. The film of claim 1, wherein the ethylene-vinyl acetate copolymer in the blend of layer b) comprises from about 14 to about 35% of vinyl acetate units.

4. The film of claim 1, wherein the ethylene/alkyl-acrylate or ethylene/alkyl-methacrylate copolymer in the blend of layer b) comprises from about 4 to about 18% by weight of alkyl-acrylate or alkyl-methacrylate derived units.

5. The film of claim 1, wherein the silicone elastomer in the blend of layer b) is polydimethylsiloxane having the composition $[-(CH_3)_2SiO-]_n$.

6. The film of claim 1, wherein the silicone elastomer is added as a masterbatch containing from about 25 to about 75% by weight of said silicone elastomer dispersed in a resin carrier.

7. The film of claim 1, wherein at least a major proportion of the outer layer b) comprises the blend of ethylene-vinyl acetate copolymer, ethylene/alkyl-acrylate or ethylene/alkyl-methacrylate copolymer, and silicone elastomer.

8. The film of claim 1, wherein outer layer b) is between about 8 and about 70 µm in thickness.

9. The film of claim 1, wherein the gas- and odour-barrier layer a) comprises vinylidene chloride copolymer with a comonomer selected from vinyl chloride, acrylic esters, acrylic acid, and blends thereof.

10. A bag or container intended in particular for use in draining and collecting excretion products from patients whose excretive apparatus has been reconstructed and/or deviated, wherein said bag or container is formed from a film according to claim 1.

* * * * *